US007423139B2

(12) United States Patent
Pecker

(10) Patent No.: US 7,423,139 B2
(45) Date of Patent: Sep. 9, 2008

(54) HIGH LEVEL EXPRESSION OF RECOMBINANT HUMAN ERYTHROPOIETIN HAVING A MODIFIED 5'-UTR

(75) Inventor: Iris Pecker, Rishon LeZion (IL)

(73) Assignee: InSight Biopharmaceuticals Ltd., Rehovot (IL)

( * ) Notice: Subject to any disclaimer, the term of this patent is extended or adjusted under 35 U.S.C. 154(b) by 505 days.

(21) Appl. No.: 10/759,031

(22) Filed: Jan. 20, 2004

(65) Prior Publication Data

US 2005/0158822 A1    Jul. 21, 2005

(51) Int. Cl.
C07H 21/00 (2006.01)
C12N 5/00 (2006.01)
C12N 15/00 (2006.01)
C07K 14/505 (2006.01)

(52) U.S. Cl. .................. 536/24.1; 536/23.51; 435/69.1; 435/320.1; 435/325; 530/397

(58) Field of Classification Search ........................ None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,703,008 A * | 10/1987 | Lin ............................ 435/360 |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 5,464,764 A | 11/1995 | Capecchi et al. | |
| 5,487,992 A | 1/1996 | Capecchi et al. | |
| 5,688,679 A | 11/1997 | Powell | |

FOREIGN PATENT DOCUMENTS

WO    WO 86/07594    12/1986

OTHER PUBLICATIONS

Wells, Additivity of Mutational Effects in Proteins. Biochemistry 29:8509-8517 (1990).*
Cone et al. "High-Efficiency Gene Transfer Into Mammalian Cells: Generation of Helper-Free Recombinant Retrovirus With Broad Mammalian Host Range", Proc. Natl. Acad. Sci. USA, 81: 6349-6353, 1984.
Jacobs et al. "Isolation and Characterization of Genomic and cDNA Clones of Human Erythropoietin", Nature, 313(6005): 806-810, 1985. Abstract.
Kozak "Influences of mRNA Secondary Structure on Initiation by Eukaryotic Ribosomes", Proc. Natl. Acad. Sci. USA, 83: 2850-2854, 1986.
Kozak "Circumstances and Mechanisms of Inhibition of Translation by Secondary Structure in Eucaryotic mRNAs", Molecular and Cellular Biology, 9(11): 5134-5142, 1989.
Kozak "Effects of Long 5' Leader Sequences on Initiation by Eukaryotic Ribosomes In Vitro", Gene Expression, 1(2): 117-125, 1991. Abstract.
Kozak "Structural Features in Eukaryotic mRNAs That Modulate the Initiation of Translation", The Journal of Biological Chemistry, 266(30): 19867-19870, 1991.
Kozak "At Least Six Nucleotides Preceding the AUG Initiator Codon Enhance Translation in Mammalian Cells", Journal of Molecular Biology, 196(4): 947-950, 1987. Abstract.
Kozak "An Analysis of 5'-Noncoding Sequences From 699 Vertebrate Messenger RNAs", Nucleic Acids Research, 15: 8125-8148, 1987.
Kozak "Context Effects and Inefficient Initiation at Non-AUG Codons in Eucaryotic Cell-Free Translation Systems", Molecular and Cellular Biology, 9(11): 5073-5080, 1989.
Kozak "The Scanning Model for Translation: An Update", The Journal of Cell Biology, 108: 229-241, 1989.
Lin et al. "Cloning and Expression of the Human Erythropoietin Gene", Proc. Natl. Acad. Sci. USA, 82: 7580-7584, 1985.
Park et al. "Efficiency of Promoter and Cell Line in High-Level Expression of Erythropoietin", Biotechnology and Applied Biochemistry, 32: 167-172, 2000.
Pelletier et al. "Insertion Mutagenesis to Increase Secondary Structure Within the 5' Noncoding Region of A Eukaryotic mRNA Reduces Translational Efficiency", Cell, 40(3): 515-526, 1985. Abstract.

* cited by examiner

*Primary Examiner*—Marianne P. Allen
*Assistant Examiner*—Regina M DeBerry

(57) ABSTRACT

The present invention provides an expression construct capable of producing high levels of erythropoietin in mammalian cells. More particularly, the expression construct includes an erythropoietin coding region fused to a unique 5'-UTR sequence and a truncated 3'-UTR. The present invention also provides methods of synthesizing large amounts of erythropoietin and in increasing serum erythropoietin level in individuals in need thereof.

11 Claims, 4 Drawing Sheets

```
 564                                         CCCCCGGTGTGGTCACCCGGCGCGCCCCAGGTCGC  599
 600 TGAGGGACCCCGGCCAGGCGCGGAGATGGGGTGCACGgtgagtactcgcgggctgggcg  659
 660 ctcccgcccgcccgggtccctgtttgagcggggatttagcgccccggctattggccaggag  719
 720 gtggctgggttcaaggaccggcgacttgtcaaggaccccggaagggggagggggtgggg  779
 780 cagcctccacgtgccagcggggacttgggggagtccttggggatggcaaaaacctgacct  839
 840 gtgaaggggacacagtttgggggttgagggggaagaaggtttgggggttctgctgtgccag  899
 900 tggagaggaagctgataagctgataacctgggcgctggagccaccacttatctgccagag  959
 960 gggaagcctctgtcacaccaggattgaagtttggccggagaagtggatgctggtagctgg 1019
1020 gggtggggtgtgcacacggcagcaggattgaatgaaggccagggaggcagcacctgagtg 1079
1080 cttgcatggttggggacaggaaggacgagctggggcagagacgtggggatgaaggaagct 1139
1140 gtccttccacagccaccct tctccctccccgctgactctcagcctggctatctgttcta 1199
1200 gAATGTCCTGCCTGGCTGTGGCTTCTCCTGTCCCTGCTGTCGCTCCCTCTGGGCCTCCCA 1259
1260 GTCCTGGGCGCCCCACCACGCCTCATCTGTGACAGCCGAGTCCTGGAGAGGTACCTCTTG 1319
1320 GAGGCCAAGGAGGCCGAGAATATCACGgtgagacccct tcccagcacattccacagaac 1379
1380 tcacgctcagggcttcagggaactcctcccagatccaggaacctggcacttggttt gggg 1439
1440 tggagctgggaagctagacactgccccccctacataagaataagtctggtggccccaaacc 1499
1500 atacctggaaactaggcaaggagcaaagccagcagatcctacggcctgtgggccagggcc 1559
1560 agagccttcagggaccct tgactccccgggctgtgtgcatttcagACGGGCTGTGCTGAA 1619
1620 CACTGCAGCTTGAATGAGAATATCACTGTCCCAGACACCAAAGTTAATTTCTATGCCTGG 1679
1680 AAGAGGATGGAGgtgagttccttttttttttttttcctttcttttggagaatctcattt 1739
1740 gcgagcctgattttggatgaaagggagaatgatcgagggaaaggtaaaatggagcagcag 1799
1800 agatgaggctgcctgggcgcagaggctcacgtctataatcccaggctgagatggccgaga 1859
1860 tgggagaattgcttgagccctggagtttcagaccaacctaggcagcatagtgagatcccc 1919
1920 catctctacaaacatttaaaaaaattagtcaggtgaagtggtgcatggtggtagtcccag 1979
1980 atatttggaaggctgaggcgggaggatcgcttgagcccaggaatttgaggctgcagtgag 2039
2040 ctgtgatcacaccactgcactccagcctcagtgacagagtgaggccctgtctcaaaaaag 2099
2100 aaaagaaaaaagaaaaataatgagggctgtatggaatacattcattattcattcactcac 2159
2160 tcactcactcattcattcattcattcattcaacaagtcttattgcataccttctgtttgc 2219
2220 tcagcttggtgcttggggctgctgaggggcaggagggagagggtgacatgggtcagctga 2279
2280 ctcccagagtccactccctgtagGTCGGGCAGCAGGCCGTAGAAGTCTGGCAGGGCCTGG 2339
2340 CCCTGCTGTCGGAAGCTGTCCTGCGGGGCCAGGCCCTGTTGGTCAACTCTTCCAGCCGT 2399
2400 GGGAGCCCCTGCAGCTGCATGTGGATAAAGCCGTCAGTGGCCTTCGCAGCCTCACCACTC 2459
2460 TGCTTCGGGCTCTGGGAGCCCAGgtgagtaggagcggacacttctgcttgccctttctgt 2519
2520 aagaaggggagaagggtcttgctaaggagtacaggaactgtccgtattccttcccttct 2579
2580 gtggcactgcagcgacctcctgttttctccttggcagAAGGAAGCCATCTCCCCTCCAGA 2639
2640 TGCGGCCTCAGCTGCTCCACTCCGAACAATCACTGCTGACACTTTCCGCAAACTCTTCCG 2699
2700 AGTCTACTCCAATTTCCTCCGGGGAAAGCTGAAGCTGTACACAGGGGAGGCCTGCAGGAC 2759
2760 AGGGGACAGATGACCAGGTGTGTCCACCTGGGCATATCCACCACCTCCCTCACCAACATT 2819
2820 GCTTGTGCCACACCCTCCCCCGCCACTCCTGAACCCCGTCGAGGGGCTCTCAGCTCAGCG 2879
2880 CCAGCCTGTCCCATGGACACTCCAGTGCCAGCAATGACATCTCAGGGGCCAGAGGAACTG 2939
2940 TCCAGAGAGCAACTCTGAGATCTAAGGATGTCACAGGGCCAACTTGAGGGCC         2991
```

Fig. 1

```
   1 TTTTCTTTTGTTTTGTTTCCACCATGGGAGTGCACGgtgagtactcgcgggctgggcgct   60
  61 cccgcccgcccgggtccctgtttgagcggggatttagcgccccggctattggccaggagg  120
 121 tggctgggttcaaggaccggcgacttgtcaaggaccccggaaggggggaggggggtggggc  180
 181 agcctccacgtgccagcggggacttgggggagtccttggggatggcaaaaacctgacctg  240
 242 tgaaggggacacagtttgggggttgaggggaagaaggtttgggggttctgctgtgccagt  300
 301 ggagaggaagctgataagctgataacctgggcgctggagccaccacttatctgccagagg  360
 361 ggaagcctctgtcacaccaggattgaagtttggccggagaagtggatgctggtagctggg  420
 421 ggtggggtgtgcacacggcagcaggattgaatgaaggccagggaggcagcacctgagtgc  480
 481 ttgcatggttggggacaggaaggacgagctggggcagagacgtggggatgaaggaagctg  540
 541 tccttccacagccacccttctccctccccgcctgactctcagcctggctatctgttctag  600
 601 AATGTCCTGCCTGGCTGTGGCTTCTCCTGTCCCTGCTGTCGCTCCCTCTGGGCCTCCCAG  660
 661 TCCTGGGCGCCCCACCACGCCTCATCTGTGACAGCCGAGTCCTGGAGAGGTACCTCTTGG  720
 721 AGGCCAAGGAGGCCGAGAATATCACGgtgagaccccttccccagcacattccacagaact  780
 781 cacgctcagggcttcagggaactcctcccagatccaggaacctggcacttggtttggggt  840
 841 ggagctgggaagctagacactgccccctacataagaataagtctggtggccccaaacca  900
 901 tacctggaaactaggcaaggagcaaagccagcagatcctacggcctgtgggccagggcca  960
 961 gagccttcagggacccttgactccccgggctgtgtgcatttcagACGGGCTGTGCTGAAC 1020
1021 ACTGCAGCTTGAATGAGAATATCACTGTCCCAGACACCAAAGTTAATTTCTATGCCTGGA 1080
1081 AGAGGATGGAGgtgagttcctttttttttttttttcctttcttttggagaatctcatttg 1140
1141 cgagcctgatttggatgaaagggagaatgatcgagggaaaggtaaaatggagcagcaga 1200
1201 gatgaggctgcctgggcgcagaggctcacgtctataatcccaggctgagatggccgagat 1260
1261 gggagaattgcttgagccctggagtttcagaccaacctaggcagcatagtgagatccccc 1320
1321 atctctacaaacatttaaaaaaattagtcaggtgaagtggtgcatggtggtagtcccaga 1380
1381 tatttggaaggctgaggcgggaggatcgcttgagcccaggaatttgaggctgcagtgagc 1440
1441 tgtgatcacaccactgcactccagcctcagtgacagagtgaggccctgtctcaaaaaaga 1500
1501 aagaaaaaagaaaaataatgagggctgtatggaatacattcattattcattcactcact 1560
1561 cactcactcattcattcattcattcattcaacaagtcttattgcataccttctgtttgct 1620
1621 cagcttggtgcttggggctgctgaggggcaggagggagagggtgacatgggtcagctgac 1680
1681 tcccagagtccactccctgtagGTCGGGCAGCAGGCCGTAGAAGTCTGGCAGGGCCTGGC 1740
1741 CCTGCTGTCGGAAGCTGTCCTGCGGGGCCAGGCCCTGTTGGTCAACTCTTCCCAGCCGTG 1800
1801 GGAGCCCCTGCAGCTGCATGTGGATAAAGCCGTCAGTGGCCTTCGCAGCCTCACCACTCT 1860
1861 GCTTCGGGCTCTGGGAGCCCAGgtgagtaggagcggacacttctgcttgccctttctgta 1920
1921 agaaggggagaagggtcttgctaaggagtacaggaactgtccgtattccttcccttcctg 1980
1981 tggcactgcagcgacctcctgttttctccttggcagAAGGAAGCCATCTCCCCTCCAGAT 2040
2041 GCGGCCTCAGCTGCTCCACTCCGAACAATCACTGCTGACACTTTCCGCAAACTCTTCCGA 2100
2101 GTCTACTCCAATTTCCTCCGGGGAAAGCTGAAGCTGTACACAGGGGAGGCCTGCAGGACA 2160
2161 GGGGACAGATGACCAGGTGTGTCC                                     2184
```

HIGH LEVEL EXPRESSION OF RECOMBINANT HUMAN ERYTHROPOIETIN HAVING A MODIFIED 5'-UTR

FIELD AND BACKGROUND OF THE INVENTION

The present invention relates to an expression construct which is capable of producing high levels of erythropoietin in mammalian cells. More particularly, the present invention relates to an expression construct which includes an erythropoietin coding region fused to a unique 5'-UTR sequence and to the use of such construct for synthesizing large amounts of erythropoietin and in increasing serum erythropoietin level in individuals in need thereof.

Erythropoietin (EPO) is produced in the adult kidney or the fetal liver in response to tissue hypoxia. Thus, a reduction of tissue oxygen level results in upregulation of the EPO gene and in increased levels of EPO in the serum. Increased levels of EPO inhibit apoptosis of the erythroid progenitor cell in the bone marrow and stimulate its proliferation and differentiation which result in a release of erythrocytes into the blood stream [Krystal, G. (1983) Exp. Hematol. 11, 649-660; Powell J S. et al. (1986) Proc. Natl. Acad. Sci. U.S.A. 83, 6465-6469]. On the other hand, lack of EPO in the serum would lead to anemia with fatigue and cellular hypoxia.

Several clinical conditions such as anemia, lung disease or cyanotic heart disease give rise to tissue hypoxia which leads to increased levels of serum EPO. However, in patients with renal insufficiency, serum EPO levels remain low in spite of hypoxia. In addition, abnormally low levels of serum EPO are also seen in anemic patients suffering from cancer, rheumatoid arthritis, HIV infection, ulcerative colitis, sickle cell anemia and anemia of prematurity.

While the causes of abnormally low levels of EPO include a primary defect in EPO production in cases of renal disease. and anemia of prematurity, and a suppression of EPO synthesis by inflammatory cytokines (e.g., IL-1, TNF-α) in cases of certain chronic diseases and cancer, administration of exogenous EPO is expected to circumvent the low levels of EPO in such conditions.

Indeed, recombinant human EPO (Rhu-EPO) has been successfully used in a variety of clinical conditions to increase production of red blood cells. Currently, erythropoietin is licensed for use in the treatment of anemia of renal failure, anemia associated with HIV infection in zidovudine (AZT) treated patients, anemia associated with cancer chemotherapy, myelodysplastic syndromes, prematurity, autologous blood donation and bone marrow transplantation [Henry, D H. and Spivak, J L. (1995). Curr. Opin. Hematol. 2: 118-124].

However, while EPO administration can benefit a wide variety of patients its use as a therapeutic agent is limited due to low production yields and high production costs.

EPO has been produced from expression vectors using transient and stable transfections in mammalian cells. These expression vectors included a 3.3 kb EPO cDNA under the control of the adenovirus major late promoter [Jacobs K et al. (1985) Nature 313, 806-809], a 5.4 kb long genomic EPO (gEPO) containing the 5' and 3' flanking regions transcribed from the simian virus 40 (SV40) promoter [Lin F K et al. (1985) Proc. Natl. Acad. Sci. U.S.A. 82, 7580-7584], a 2.4 kb ApaI fragment of the EPO gene containing 58 bp of the 5' UTR (U.S. Pat. No. 5,688,679 to Powell, J. S., 1986), and a 5' and 3' UTR-deleted EPO genomic clone (Park, J. H. et al., Biotechnol. Appl. Biochem. (2000) 32: 167-72). However, these transfections resulted in relatively low yields of EPO, which varied between 2-7 IU/ml EPO in 48 hours when the transcribed sequence included 5' and 3' flanking regions, to 56-68 IU/ml in 48 hours when truncated 5'-UTR or UTR-deficient EPO constructs were utilized.

There is thus a widely recognized need for, and it would be highly advantageous to have, an expression system capable of producing high levels of EPO devoid of the above limitations.

SUMMARY OF THE INVENTION

According to one aspect of the present invention there is provided a chimeric polynucleotide comprising a nucleic acid sequence encoding an erythropoietin polypeptide attached to a 5'-UTR sequence as set forth by SEQ ID NO:6 or 7.

According to another aspect of the present invention there is provided a nucleic acid construct comprising the chimeric polynucleotide.

According to yet another aspect of the present invention there is provided a eukaryotic cell culture genetically modified to produce at least 150 international units of erythropoietin per milliliter medium per 48 hours.

According to still another aspect of the present invention there is provided a method of increasing blood erythropoietin level in an individual in need thereof comprising expressing in cells of the individual a polynucleotide including a nucleic acid sequence encoding an erythropoietin polypeptide attached to a 5'-UTR sequence as set forth by SEQ ID NO:6 or 7 to thereby increase blood erythropoietin level in the individual.

According to further features in preferred embodiments of the invention described below, the nucleic acid sequence includes an adenine as part of a guanine-guanine-adenine triplet encoding glycine at position 2 of SEQ ID NO:10.

According to still further features in the described preferred embodiments the chimeric polynucleotide further includes at least 10 and no more than 15 non-translatable nucleic acids attached to a 3' end of the nucleic acid sequence.

According to still further features in the described preferred embodiments the nucleic acid sequence further includes 12 non-translatable nucleic acids attached to a 3' end of the nucleic acid sequence.

According to still further features in the described preferred embodiments the nucleic acid sequence is set forth by SEQ ID NO:11.

According to still further features in the described preferred embodiments the nucleic acid sequence is set forth by SEQ ID NO:12.

According to still further features in the described preferred embodiments the nucleic acid construct further comprising a promoter for directing expression of the chimeric polynucleotide in eukaryotic cells.

According to still further features in the described preferred embodiments the nucleic acid construct further comprising a promoter for directing expression of the chimeric polynucleotide in mammalian cells.

According to still further features in the described preferred embodiments the promoter is selected from the group consisting of SV40 promoter, CMV promoter, adenovirus major late promoter, Rous sarcoma virus promoter.

According to still further features in the described preferred embodiments the nucleic acid construct further comprising a dihydrofolate reductase expression cassette positioned under a control of a thymidine kinase promoter.

According to still further features in the described preferred embodiments the cells are of a mammalian origin.

According to still further features in the described preferred embodiments the cells are ex-vivo transfected with a mammalian expression vector including the polynucleotide positioned under the control of a mammalian promoter.

According to still further features in the described preferred embodiments expressing is effected by providing to the individual a mammalian expression vector including the polynucleotide positioned under the control of a mammalian promoter.

The present invention successfully addresses the shortcomings of the presently known configurations by providing an expression construct which is capable of producing high levels of erythropoietin in mammalian cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a nucleotide sequence of the cloned erythropoietin genomic DNA fragment (SEQ ID NO:8) utilized by the pC2-B3 plasmid. The numbers correspond to an EPO published genomic sequence (GenBank Accession No. M11319, Lin et al., 1985). Exons appear in uppercase letters while introns are in lowercase letters. Coding sequences are underlined, the translation start site and stop codon appear in bold letters. The deviations from the published sequence (an additional C at position 667, a T to C substitution at position 1445 and a G to A substitution at position 1775) are marked with bold-italics letters.

FIG. 4 is a nucleotide sequence of the cloned erythropoietin genomic DNA (SEQ ID NO:9) as positioned in the pASC2M-TKdhfr expression vector. Exons appear in uppercase letters while introns are in lowercase letters. Coding sequences are underlined, translation start site and stop codon appear in italics. The modified nucleotides at the 5' end are bolded.

DESCRIPTION OF THE PREFERRED EMBODIMENTS

Figure 2:
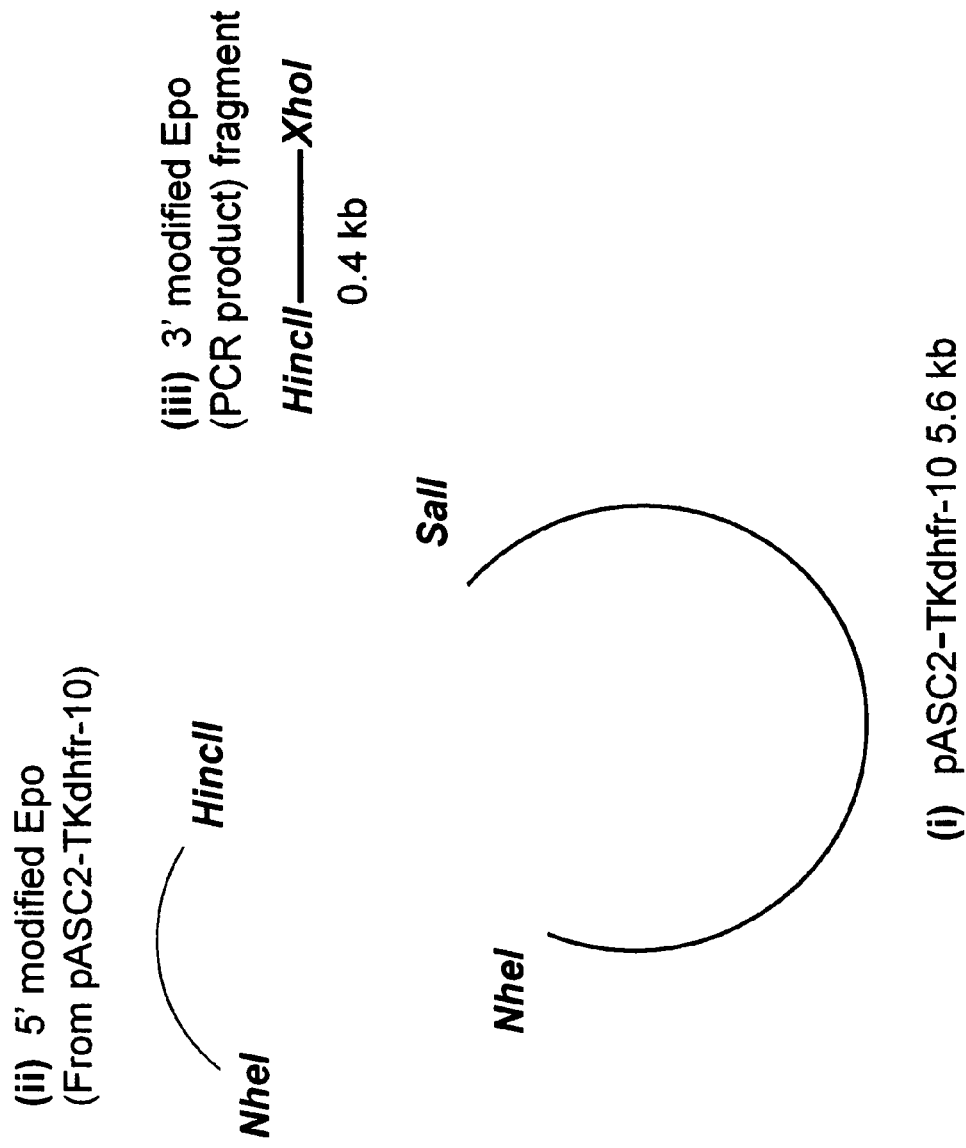
FIG. 2 is a schematic illustration depicting assembly of the pASC2M-TKdhfr-8 expression vector. The pASC2M-TKdhfr-8 plasmid was constructed by tri-partite ligation of the following fragments: a 5.6 kb fragment containing the pSI vector with the dhfr expression cassette, devoid of the chimeric intron (derived from digestion of pASC2-TKdhfr-10 with NheI and SalI), a 1.8 kb fragment containing the 5' of the EPO genomic sequence with the minimal 5' UTR (derived from pASC2-TKdhfr-10 digested with NheI and HincII), and a 0.4 kb fragment containing the 3' portion of the EPO genomic sequence with a short 3' UTR (derived from the U1U-C2min3 PCR product digested with HincII and XhoI).

The present invention is of a chimeric polynucleotide encoding EPO which is capable of producing high levels of EPO in mammalian cells and can be used to treat disorders which are associated with, or lead to, abnormal EPO production such as, anemia.

The principles and operation of the chimeric polynucleotide encoding EPO according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Erythropoietin (EPO) is a glycoprotein hormone which regulates the production of erythrocytes from the erythroid progenitor cell in the bone marrow. EPO is produced in the adult kidney or the fetal liver in response to tissue hypoxia. High levels of EPO in the serum inhibit apoptosis of the erythroid progenitor cell in the bone marrow and promote its proliferation and differentiation to release erythrocytes into the blood stream.

Recombinant EPO has been used for reversing anemia caused by disorders such as renal failure, HIV infection in zidovudine (AZT) treated patients, cancer chemotherapy, myelodysplastic syndromes, prematurity, autologous blood donation and bone marrow transplantation [Henry, D H. and Spivak, J L. (1995). Curr. Opin. Hematol. 2: 118-124].

Previous attempts to produce recombinant human EPO have resulted in poor yields of this commercially important protein.

While reducing the present invention to practice, the present inventor has constructed a chimeric polynucleotide encoding EPO that produces at least 150 IU/ml EPO in 48 hours when expressed in mammalian cells, thus substantially improving synthesis yields as compared to prior art EPO expression systems.

Thus, according to one aspect of the present invention there is provided a chimeric polynucleotide comprising a nucleic acid sequence encoding an erythropoietin polypeptide attached to a 5'-UTR sequence as set forth by SEQ ID NO:6 or 7.

As used herein, the phrase "chimeric polynucleotide" refers to a polynucleotide sequence which includes sequences from different genes or different species. Accordingly, a chimeric polynucleotide may comprise regulatory sequences and coding sequences that are derived from different species, or regulatory sequences and coding sequences that are derived from the same species, but are arranged in a manner different than that found in nature.

As used herein the term erythropoietin (EPO) polypeptide refers to the human EPO protein (GenBank Accession number: NP_000790) which is set forth by SEQ ID NO:10. The EPO polypeptide can be encoded by a naturally occurring or synthetic polynucleotide which may or may not include intronic sequences.

The nucleic acid sequence of the present invention can be a complementary or genomic DNA fragment which is at least 90%, at least 95%, more preferably, 98% or more homologous to the polynucleotide sequence set forth by SEQ ID NO:11 (in the case of cDNA) or 12 (in the case of a genomic fragment), as determined using the BlastN software of the National Center of Biotechnology Information (NCBI) using default parameters.

Examples of naturally occurring nucleic acid sequences which encode EPO include, but are not limited to, the human EPO coding sequence (GenBank Accession number: NM_000799) or any of its homologues such as rat EPO (GenBank Accession number: NM_017001), mouse EPO (GenBank Accession number: NM_007942) or ox EPO (GenBank Accession number: NM_173909). Synthetic polynucleotide sequences which encode a polypeptide at least 75%, preferably at least 80%, more preferably at least 85%, most preferably 90%-100% homologous to SEQ ID NO:10 as determined by the BlastP software of the National Center of Biotechnology Information (NCBI) using default parameters can also be used by the present invention to generate EPO.

As is mentioned hereinabove, the chimeric polynucleotide of the present invention is designed to express high levels of EPO in mammalian cells.

It will be appreciated that the expression level of a recombinant gene in mammalian cells depends on several factors such as transcriptional control elements, integration position, gene copy number, translational efficiency, 5' and 3' untranslated regions (UTRs) and other factors.

The translational efficiency depends in part on proper splicing, mRNA stabilization (e.g., via capping of the first nucleotide of the RNA transcript and/or polyadenylation at the 3'-UTR), and initiation of translation by the ribosomal complex at the AUG initiation codon. Initiation of translation depends on several features of the sequence upstream of the main initiation site which is further referred to as a leader sequence or a 5'-UTR sequence, hereinbelow. For example, the nucleotide sequence surrounding the AUG codon (Kozak, M., 1987. Nucleic Acids Res. 15: 8125-8148; Kozak, M., 1987. J. Mol. Biol. 196: 947-950; Kozak, M., 1989. Mol. Cell. Biol.9: 5073-5080), the length of the leader sequence (Kozak, M. 1991. Gene. Exp. 1: 117-125; , Kozak, M. 1991. J. Biol. Chem266: 19867-19870), the secondary structure in the leader sequence (Pelletier, J. and Sonenberg, N. 1985. Cell. 40: 515-526 ; Kozak, M. 1986. Proc. Natl. Acad. Sci. USA. 83: 2850-2854; Kozak, M. 1989. Mol. Cell. Biol. 9: 5134-5142) and the presence of additional AUG codons upstream of the main initiation site (Kozak, M., 1989. J. Cell Biol. 108: 229-241; Futterer, J. and Hohn, T. 1992. Nucleic Acids Res. 20: 3851-3857) can affect the probability of translation initiation at a specific AUG codon.

Thus, the chimeric polynucleotide of the present invention includes UTR sequences specifically designed capable of improving translational efficiency of fused EPO coding sequences in eukaryotic cells.

Suitable 5'-UTR sequences for use with the present invention were selected using theoretical sequence analyses and/or experimental methods employing tools such as those available via the Institute of Cytology and Genetics, The Siberian Branch of the Russian Academy of Science (wwwmgsdotbionetdotnscdotru/mgs/programs/leadermrna/ma_mrna_edothtml).

The result of the above describe analysis is described in Example 1 which illustrates a unique UTR sequence (TTTTCTTTTGTTTTGTTTCCACC, SEQ ID NO:6) suitable for use with the present invention.

Another approach for increasing the translation activity of the chimeric polynucleotide of the present invention is via the reduction of the guanine and cytosine content of the sequence following the translation initiation.

Thus, according to a preferred embodiment of the present invention, at least one guanine or cytosine nucleotides in the sequence following the AUG initiation codon are replaced with at least one adenine or cytosine nucleotides. It will be appreciated that such a nucleotide change may result in an amino acid change in the translated polypeptide unless a wobble nucleotide is replaced. Those of skills in the art are capable of selecting such nucleotide modifications that do not affect the amino acid sequence of the translated polypeptide.

As is shown in Example 1 of the Examples section which follows a guanine to adenine substitution was introduced at the wobble nucleotide (i.e., the third guanine nucleotide of the guanine-guanine-guanine triplet) encoding Glycine at position 2 of the EPO polypeptide as set forth by SEQ ID NO:10.

Once selected, the new leader sequence or the modified sequence following the translation initiation codon are incorporated into the chimeric polynucleotide encoding EPO via, for example, site directed mutagenesis.

Methods of introducing site directed mutations are known in the art and include, for example, PCR directed mutagenesis. Briefly, a PCR reaction is performed on a DNA template using primers which are selected from the DNA template but include modified, deleted or added nucleotides in order to direct the PCR reaction to generate a mutated sequence. The PCR conditions are usually adjusted to amplify the template using the modified primers. Such adjustments include for example, increasing the concentration of the magnesium chloride ions and/or reducing the annealing temperature and the selection of suitable PCR conditions are within the capabilities of one skilled in the art.

As was previously shown, production of EPO was increased when the 3'-UTR sequence thereof was truncated (Park, J. H. et al., 2000. Biotechnol. Appl. Biochem. 32: 167-72).

Thus, according to preferred embodiments the chimeric polynucleotide of the present invention further includes at least 10 and no more than 15, more preferably, at least 11 and no more than 14, most preferably, 12 non-translatable nucleic acids attached to a 3' end of the nucleic acid sequence encoding EPO.

It will be appreciated that the sequence at the 3'-UTR can be truncated via PCR directed mutagenesis as described hereinabove. As is further shown in Example 1 of the Examples section which follows, using the C2min3 primer (SEQ ID NO:5) the present inventor has shortened the 3'-UTR of the polynucleotide encoding EPO to contain only 12 nucleotides following the TGA translation stop codon.

Altogether, as is shown in Example 2 of the Examples section which follows, the modifications introduced into the chimeric polynucleotide encoding EPO of the present invention [i.e., the unique 5'-UTR sequence (SEQ ID NO:6), the guanine to adenine substitution at the wobble nucleotide encoding the Glycine at position 2 of the EPO polypeptide and the truncated 3'-UTR sequence] resulted in high expression level of EPO in the range of 140-157 IU/ml in 48 hours.

The chimeric polynucleotide of the present invention can be used to produce the EPO polypeptide via in vitro transcription-translation systems or preferably by transfecting cells with an expression vector containing the chimeric polynucleotide of the present invention.

According to preferred embodiments the chimeric polynucleotide of the present invention is ligated into an expression vector which includes a promoter suitable for directing expression of the EPO polypeptide in mammalian cells.

Constitutive promoters suitable for use with the present invention are promoter sequences which are active under most environmental conditions and most types of cells such as the CMV promoter, SV40 promoter, adenovirus major late promoter and Rous sarcoma virus (RSV).

The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or RSV and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned at approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of EPO mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

The expression vector of the present invention can be used to express the recombinant EPO polypeptide in mammalian cells (e.g., HeLa cells, Cos cells), yeast cells (e.g., AH109, HHY10, KDY80), insect cells (e.g., Sf9) or bacteria cells (e.g., JM109, RP437, MM509, SW10).

Preferably, the EPO polypeptide of the present invention is synthesized by ligating the chimeric polynucleotide (e.g., the polynucleotide set forth by SEQ ID NO:9) into a mammalian, yeast or bacterial expression vector. Examples of such vectors include but are not limited to the pcDNA3.1, pBK-CMV and pCI vectors which are suitable for use in mammalian cells, the pGBKT7, pLGAD H2-lacZ and pBGM18 vectors which are suitable for use in yeast cells and the pACK02scKan, pML-BAD, pMLS7 vectors which are suitable for use in bacterial cells.

Since the immature human EPO polypeptide (SEQ ID NO:10) is subjected to several post-translational modifications including the cleavage of both a 27 amino acid signal peptide at the N-terminal and an arginine residue at the C-terminal, and the addition of three asparagine (N)-linked tetraantennary oligosaccharides [Dordal M. S., et al. (1985). The role of carbohydrate in erythropoietin action. Endocrinology. 116: 2293-9; Wasley, L. C., et al. (1991) Blood 77: 2624-2632] the expression vector of the present invention is preferably constructed for eukaryotic expression, most preferably, mammalian cell expression.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRepS, D H26S, D HBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of the present invention into mammalian cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods. For example, for stable transfection in dihydrofolate reductase deficient Chinese Hamster Ovary (CHO dhfr-) cells the expression vector of the present invention further includes a dihydrofolate reductase expression cassette positioned under a control of a thymidine kinase promoter.

Introduction of nucleic acids by viral infection offers several advantages over other methods such as lipofection and electroporation, since higher transfection efficiency can be obtained due to the infectious nature of viruses.

Once produced in a host cell, the recombinant EPO protein is secreted into the culture medium and preferably purified from conditioned medium using for example, ion exchange and reverse phase chromatography as described in WO Pat. Appl. No. 86/07594 to Por-Hsiung, L. and Strickland, T.

Purified EPO protein can be further tested for their specific activity using methods known in the art, including for example determining the incorporation of $^{59}$Fe into circulating red blood cells of polycythaemic mice which have been exposed to reduced atmospheric pressure, essentially as described elsewhere (European Pharmacopoeia, $4^{th}$ edition, Directorate for the Quality of Medicines of the Council of Europe, 2002 pp. 1127-8).

As is mentioned hereinabove, EPO induces proliferation and differentiation of the erythroid progenitor cell. Such an effect on the erythroid progenitor cell can be tested by employing the EPO polypeptide of the present invention on methylcellulose bone marrow cultures and scoring the size and number of burst-forming unit-erythroid (BFU-E) colonies as described elsewhere (Martiney, J. A. et al., 2000. Anemia. Infect. Immun. 68: 2259-2267).

The purified EPO polypeptide of the present invention can be used to treat the anemia associated with renal failure, HIV infection in zidovudine (AZT) treated patients, cancer chemotherapy, myelodysplastic syndromes, prematurity, autologous blood donation and bone marrow transplantation as reviewed by Henry, D H. and Spivak, J L., 1995 (Clinical use of erythropoietin. Curr. Opin. Hematol. 2: 118-124).

Since the chimeric polynucleotide of the present invention is capable of expressing EPO in mammalian cells it can be used in in-vivo or ex-vivo therapy of disorders requiring EPO.

Thus, according to another aspect of the present invention there is provided a method of increasing blood EPO level in an individual in need thereof.

As used herein the phrase "increasing blood EPO level" refers to the production of EPO polypeptides in individuals with low EPO levels in the serum which suffer from anemia and/or tissue hypoxia.

According to preferred embodiments of the present invention the method is effected by expressing in cells of the individual the chimeric polynucleotide of the present invention to thereby increase blood EPO level in the individual.

Such expressing can be effected by ex vivo transfection of cells of the individual with a mammalian expression vector including the chimeric polynucleotide positioned under the control of a mammalian promoter and subsequent administration of the transfected cells into the blood stream or tissue of the individual.

As is used herein the term "cells" refers to bone marrow cells, stem cells of various cell lineages (e.g., hematopoietic, stromal, epithelial), kidney cells, fetal or adult liver cells, smooth muscle cells, endothelial cells which are obtained from the individual via for example fine needle aspiration or a biopsy. The cells of the present invention are isolated from the individual and are optionally cultured under suitable culturing conditions.

For example, if bone marrow cells are utilized, such cells can be obtained by aspiration from the iliac crest, femora, tibiae, spine, rib or other medullar spaces and low-density marrow cells (<1.077 g/cm$^3$) are isolated by density-cut separation on Ficoll-Hypaque (Pharmacia, Piscataway, N.J.). Progenitor cells are enriched from the low-density marrow cells as described elsewhere (Broxmeyer, H. E. et al., 1991, J. Immun., 147: 2586-2594), and are plated at $10^5$ cells/ml in 1% methylcellulose cultures supplemented with suitable growth factors, including, for example, EPO (1 U/ml), recombinant human interleukin-3 (rhu IL-3, 100 U/ml, Immunex Corp., Seattle, Wash.) and recombinant human steel factor (50 ng/ml, Immunex Corp.). Cultures are maintained in a humidified atmosphere of 5% $CO_2$ in lowered (5%) oxygen at 37° C.

As is used herein the phrase "ex vivo transfection" refers to transfection of the cells with an expression vector including the chimeric polynucleotide which is designed for expressing EPO in such cells.

The expression vector described above can be delivered into the cells using a variety of delivery approaches, including, but not limited to, microinjection, electroporation, liposomes, iontophoresis or receptor-mediated endocytosis. The selection of a particular method will depend, for example, on the cell into which the chimeric polynucleotide is to be introduced.

It will be appreciated that in order to increase blood EPO levels the transfected cells are administered to the individual in need thereof.

Administration of the cells of the present invention can be effected using any suitable route such as intravenous, intra peritoneal, intra hepatic, intra spleenic, intra pancreatic, subcutaneous, transcutaneous, intramuscular, intracutaneous, and/or injection in smooth muscle, using e.g., a catheter.

The cells of the present invention can be derived from either autologous sources such as self bone marrow cells or from allogeneic sources such as bone marrow derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly (allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002, 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002, 13: 783-96). Moreover, nanoporous biocapsules with well-controlled pore size as small as 7 nm, tailored surface chemistries and precise microarchitectures were found to successfully immunoisolate microenvironmrients for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

According to preferred embodiments of the present invention expressing is effected by providing to the individual a mammalian expression vector including the chimeric polynucleotide encoding EPO positioned under the control of a mammalian promoter.

The expression vector including the chimeric polynucleotide encoding EPO can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the expression vector encoding EPO which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran.

Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the expression vector including the chimeric polynucleotide encoding EPO of the present invention) effective to prevent, alleviate or ameliorate symptoms of a disorder (e.g., anemia and/or tissue hypoxia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to prevent anemia and/or tissue hypoxia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the expression vector of the invention formulated in a compatible pharmaceutical carrier may also be prepared, placed in an appropriate container, and labeled for treatment of an indicated condition, as if further detailed above.

According to a preferred embodiment of the present invention, the expression vector including the chimeric polynucleotide encoding EPO of the present invention is administered into host tissues using a viral carrier.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the type transformed. The ability to select suitable vectors according to the cell type transformed is well within the capabilities of the ordinary skilled artisan and as such no general description of selection consideration is provided herein.. For example, bone marrow cells can be targeted using the human T cell leukemia virus type I (HTLV-I).

Recombinant viral vectors are useful for in vivo expression of the chimeric polynucleotide of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

When retroviruses, for example, are used for polynucleotide transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

Mammalian cell systems which utilize recombinant viruses or viral elements to direct expression can be engineered. For example, when using adenovirus expression vectors, the chimeric polynucleotide encoding EPO can be ligated to an adenovirus transcription/translation control complex, e.g., the late promoter and tripartite leader sequence. Alternatively, the vaccinia virus 7.5K promoter can be used (Mackett et al., Proc. Natl. Acad. Sci., USA 79:7415-7419, 1982; Mackett et al, J. Virol. 49:857-864, 1984; Panicali et al., Proc. Natl. Acad. Sci., USA 79:4927-4931, 1982).

Particularly useful are bovine papilloma virus vectors, which can replicate as extrachromosomal elements (Sarver et al., Mol. Cell. Biol. 1:486, 1981). Shortly after entry of this DNA into mouse cells, the plasmid replicates to about 100 to 200 copies per cell. Transcription of the inserted cDNA yielding a high level of expression may result without integration of the plasmid into the host cell chromosome. These vectors can be used for stable expression by including a selectable marker in the plasmid, such as, for example, the neo gene. Alternatively, the retroviral genome can be modified for use as a vector capable of introducing and directing the expression of the chimeric polynucleotide encoding EPO in the host cells (Cone and Mulligan, Proc. Natl. Acad. Sci., USA 81:6349-6353, 1984). High level expression can also be achieved using inducible promoters, including, but not limited to, the hypoxia-inducible factor (HIF)-I alpha promoter.

Additional expression vectors containing regulatory elements from eukaryotic viruses such as retroviruses include the SV40 vectors (e.g., pSVT7 and pMT2), the bovine papilloma virus vectors (e.g., pBV-1MTHA) and vectors derived from Epstein Bar virus (e.g., pHEBO and p205). Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

It will be appreciated that the expression of the chimeric polynucleotide encoding EPO of the present invention can be specifically expressed in blood cells by placing the chimeric polynucleotide sequence under the transcriptional control of an erythroid specific promoter such as the promoter of BVL-1-like VL30 promoter (Staplin W R and Knezetic J A, 2003. BVL-1-like VL30 promoter sustains long-term expression in erythroid progenitor cells. Blood 101: 1798-800).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes 1-111 Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Construction of a 5'-UTR Modified Erythropoietin Expression Vector

In order to produce large quantities of erythropoietin (EPO) a chimeric polynucleotide containing a genomic sequence encoding human EPO flanked by a modified 5'-UTR and a 12-nucleotide 3'-UTR was constructed in an expression vector containing the mouse dihydrofolate reductase (dhfr) expression cassette for stable clone selection in Chinese Hamster Ovary (CHO) cells.

Materials and Experimental Methods

Cell lines—Chinese Hamster Ovary dihydrofolate reductase deficient (CHO dhfr-) cells were maintained in F12 medium (Invitrogen, life technologies, Frederick, Md., USA) supplemented with 10% fetal bovine serum (FBS, Invitrogen, life technologies).

Extraction, manipulation and analysis of DNA—Plasmid DNA was extracted from E. Coli cells using the plasmid mini kit (Cat. No. 27106, Qiagen, CA USA) or plasmid midi kit (Cat. No. 12145, Qiagen). DNA restriction analysis was performed using restriction enzymes manufactured by New England Biolabs according to the manufacturer's recommendations. DNA was electrophoresed on Tris-Boric acid-EDTA (TBE) agarose gels and Ethidium bromide stained gels were documented by the Gel Doc 2000™ gel documentation system (BioRad, Hercules, Calif. USA) according to the manufacturer's instructions. PCR reactions were performed using a high fidelity enzyme Bio-X-Act (Bio-21049, Bioline, Randolph, Mass. USA) or by Expand high fidelity (Cat. No. 3 300 242, Roche Applied Science, Penzberg, Germany). DNA sequencing was performed using the BigDye Terminator cycle sequencing kits (Applied Biosystems, Foster City, Calif. USA) according to manufacturer's instruction and extension reactions were electrophoresed and analyzed on the 377 DNA sequencer (Applied Biosystems) at the Weizmann Institute of Science, Rehovot, Israel.

Experimental Results

Cloning of the human erythropoietin gene—To clone the human erythropoietin (EPO) gene human male genomic DNA (G1471 Lot: 157888, Promega, Corp., Madison, Wis., USA) was subjected to PCR amplification using the high fidelity enzyme Bio-X-Act (Bio-21049, Bioline, Randolph, Mass. USA) and the U1U and U1L PCR primers (Table 1, hereinbelow) which were selected from the 5'-UTR and 3'-UTR sequences, respectively, of the EPO coding sequence. The PCR primers were designed to contain the EcoRI and NaeI restriction recognition sites at the 5' and 3'-ends, respectively. The resultant 2.4 Kb PCR product was subcloned into the EcoRI and EcoR V recognition sites of the pBluescript SK- (Stratagene, La Jolla, Calif.) plasmid which was designated as pC2-B3. Sequencing of the pC2-B3 plasmid confirmed the presence of five EPO exons intervened by four introns and flanked by 61 nucleotides of the 5'-UTR and 220 nucleotides of the 3'-UTR. Comparison of the sequence generated from the pC2-B3 plasmid with a published sequence of human erythropoietin (GenBank Accession No. M11319, Lin et al., 1985. Proc. Natl. Acad. Sci. U.S.A. 82: 7580-7584) revealed two polymorphisms in intronic sequences (insertion of C at position 667 and a G→A substitution at position 1775) as well as a T→C substitution at position 1445 which probably reflects a PCR-derived spontaneous mutation in an intronic sequence. Construction of Erythropoietin/pSI plasmid (pSIC2)—The full-length genomic fragment (2.4 kb) containing the EPO genomic coding sequence was excised from pC2-B3 plasmid using the EcoRI and SalI restriction enzymes and was further ligated into the pSI plasmid (Promega, Madison, Wis. USA) using the EcoRI and SalI cloning sites. The resultant EPO clone was designated pSIC2. Construction of a modified 5'UTR EPO plasmid (pSC2-2)—To improve the translation efficiency of the recombinant EPO a modified 5' UTR was designed using the translation efficiency algorithm predicting high/low mRNA expression of a mammalian gene (AV. Kochetov, Institute of Cytology and Genetics SD RAS, Russia) available through Wwwmgsdot-bionetdotnscdotru/mgs/programs/leadermrna/ma_mrna_e-dothtml. The selected sequence was introduced into the Syn5 primer (Table 1, hereinbelow) which together with the LPG2 primer which corresponds to nucleotides 1416-1440 at the 3' end used to amplify the new 5'-UTR region. In order to increase the translation efficiency the GC content was reduced by introducing via the SynS primer a guanine to adenine (G→A) substitution at the third position of the guanine-guanine-guanine triplet encoding glycine at position 2 of SEQ ID NO:10 (see underlined A in SEQ ID NO:3, Table 1, hereinbelow). PCR was performed using pSIC2 plasmid as template DNA and the resultant PCR product was blunt ended using T4 DNA polymerase and was digested with XbaI. In parallel, the pSIC2 plasmid DNA was digested with EcoRI, blunt ended and digested with XbaI. The two DNA fragments were ligated and the resultant plasmid was designated as pSC2-2. Further sequence analysis of the pSC2-2 plasmid revealed the following 5'-UTR sequence: TTTTCTTTTGTTTTGTTTCCACC (SEQ ID NO:6) which is 15-nucleotides shorter at the 5' end than the 5'-UTR sequence introduced in the Syn5 primer: AAT-TCTTTTGTTTTGTTTTCTTTTGTTTTGTTTCCACC which is set forth by SEQ ID NO:7. The I 5-nucleotides deletion was generated by either residual double strand exonucleolytic activity of the T4 DNA polymerase or by a recombination event occurred in the E. Coli host cell due to the presence of a highly repetitive sequence. Since the shorter sequence was still scored as having a high translation potential using the translation predicting algorithm is was selected for further use.

Excision of a chimeric intron in the pSI plasmid—A chimeric intron located downstream of the SV40 promoter in the pSI plasmid is designed to improve the expression of cDNAs. Since this intron was assumed to be redundant in expression of genomic sequences containing endogenous introns it was excised by digestion of the pSC2-2 plasmid with AflII restriction enzyme followed by self-ligation. The resultant plasmid was designated pASC2-6.

Insertion of tile TKdhfr into tile EPO expression plasmid (pASC2-10TKdhfr)—A dhfr expression cassette was constructed in the plasmid pRL-TK (E2241 Lot: 158375, Promega) by replacing the Luciferase cDNA with the cDNA of mouse dhfr (Accession No. NM_010049, SEQ ID NO:13). The Luciferase cDNA was excised from the pRL-Tk using the NheI and XbaI restriction enzymes. The cDNA of mouse dhfr previously subcloned in the HindIII and BamHI sites of Blue-Script SKII (Stratagene) plasmid was excised using the HindIII and XbaI restriction enzymes. The NheI and HindIII sticky ends were blunted prior to digestion with the second enzyme. pRL-TK was ligated with the mouse dhfr cDNA fragment and the resultant plasmid was designated pRL-TKdhfr2. In the pRL-TKdhfr2 plasmid the mouse dhfr cDNA was cloned downstream of the relatively weak constitutive promoter sequence of HSV-thymidine kinase and upstream of the SV40 late polyadenylation signal. The dhfr expression cassette was excised from the pRL-TKdhfr-2 plasmid using the BglII and BamHI restriction enzymes and was cloned into the BamHI site of the pASC2-6 plasmid. The resultant plasmid was designated: pASC2-TKdhfr-10. The TKdhfr expression cassette was similarly inserted into the control vector pC2 to generate the control vector pC2-TKdhfr Modification of 3'UTR—The 3'UTR of the EPO fragment was shortened to contain only 12 nucleotides downstream of the translation stop codon using the U1U 5'-primer and the C2min3 modified 3'-UTR primer (Table 1, hereinbelow), which overlaps the translation stop codon. The resultant modified 3' sequence was 208 bp shorter than the original 3' fragment.

TABLE 1

PCR primers

| Primer name | SEQ ID NOs. | Forward (F) and reverse (R) primers (5'→3') |
|---|---|---|
| U1U | SEQ ID NO:1 F: | ATGAATTCCCCCGGTGTGGTCACCC |
| U1L | SEQ ID NO:2 R: | CATGCCGGCCCTCAAGTTGGCCCTG |

TABLE 1-continued

PCR primers

| Primer name | SEQ ID NOs. | Forward (F) and reverse (R) primers (5'→3') |
|---|---|---|
| Syn5 | SEQ ID NO:3 F: | AATTCTTTTGTTTTGTTTTCTTTTGTTTTGTTTCCACCATGGGAGTGCACGGTGAGT |
| LPG2 | SEQ ID NO:4 R: | ACCCCAAACCAAGTGCCAGGTTCCT |
| C2min3 | SEQ ID NO:5 R: | TACTCGAGGACACACCTGGTCATCTGTC |

Figure 3:
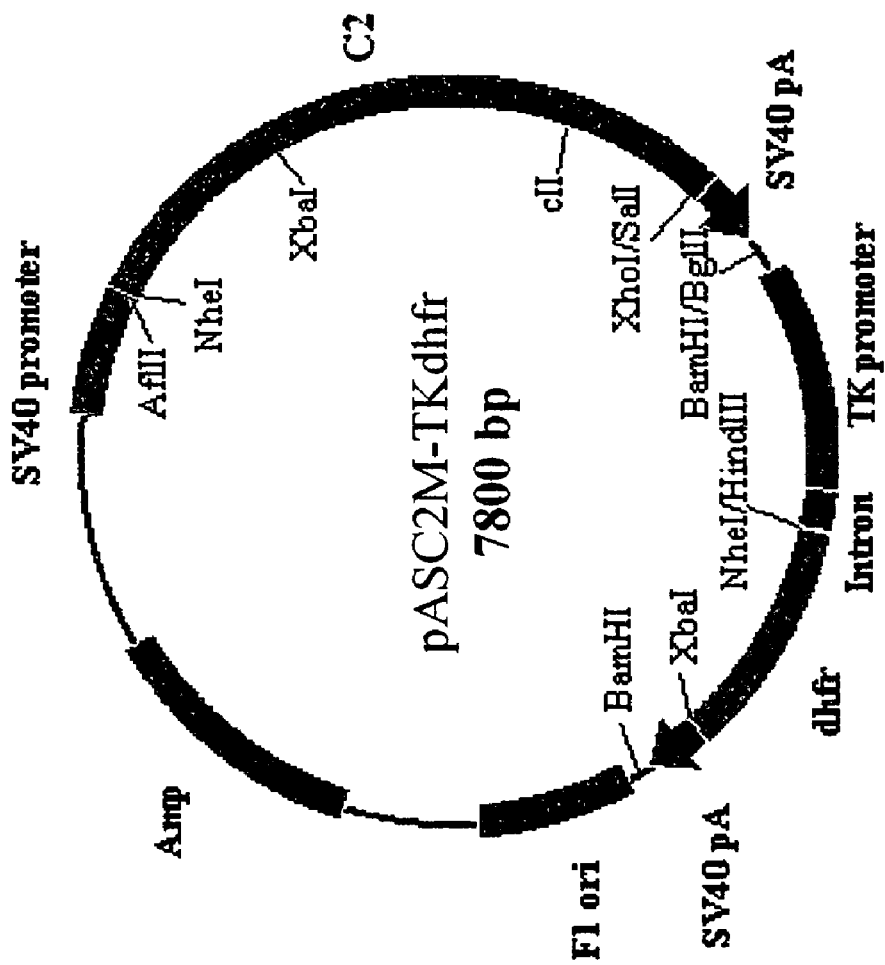
FIG. 3 is a schematic illustration of the pASC2M-TKdhfr EPO expression vector; functional domains and restriction sites used for construction are indicated.

Table 1: Sequences of PCR primers. Bolded ATG (in SEQ ID NO:3) = translation start site; underlined A (in SEQ ID NO:3) = silent Glycine point mutation; bolded TCA (in SEQ ID NO:5) = termination codon;

Assembly of the EPO expression vector—The EPO expression vector (pASC2M-TKdhfr-8) was constructed by tri-partite ligation as is shown in FIG. 2. To reveal the vector fragment the pASC2-TKdhfr-10 plasmid (an intermediate vector containing a pSI plasmid, deletion of the chimeric intron, an EPO sequence with a modified 5' UTR and a dhfr expression cassette) was digested with the NheI and SalI restriction enzymes. The resultant 5.6 Kb fragment contained the pSI vector devoid of the chimeric intron, and the dhfr expression cassette. To reveal the modified 5'-UTR fragment the pASC2-TKdhfr-10 was digested with NheI and HincII and a 1.8 kb fragment-as obtained. To reveal the modified 3' EPO fragment the U1U-min3 PCR product was digested with HincII and XhoI and a 0.4 kb fragment was obtained. Sequencing of the EPO sequence from the resultant pASC2M-TKdhfr-8 expression vector (FIG. 3) confirmed the tri-partite ligation and is presented in FIG. 4.

These results demonstrate the construction of an expression vector containing the EPO genomic sequence with a modified 5'-UTR and a 12-nucleotide 3'-UTR sequences and a dhfr expression cassette.

Example 2

CHO Cells Transfected With the 5'-UTR Modified EPO Expression Vector Express High Level of Erthropoietin The 5'-UTR modified EPO expression vector was transiently transfected in CHO dhfr- cells and high levels of erythropoietin were secreted into the medium.

Materials and Experimental Methods

Transfections—For DNA transfection 3×10⁶ CHO dhfr- cells were seeded in 6-well plates and following one day of incubation were transfected with 2.5 μg plasmid DNA in 6 μl Fugene reagent (Roche, Indianapolis, Ind., USA) according to manufacturer's recommendations. For each construct the transfection was performed in triplicates.

Immunoassay—The quantity of secreted recombinant EPO was determined in media samples collected 48 hours post-transfection using the Quantikine (R&D Systems, Minneapolis, Minn. USA) immunoassay for human Erythropoietin, according to the manufacturer instructions.

Experimental Results

Recombinant EPO with modified 5'-UTR and minimal 3'-UTR region produces high levels of EPO in CHO transiently transfected cells—CHO cells were transiently transfected with the control vector (pC2-TKdhfr, Table 2, hereinbelow) containing an ApaI genomic fragment which contains the EPO coding sequence (as described in U.S. Pat. No. 5,688,679 to Powell, J. S., 1986) with the pSI expression vector including the dhfr expression cassette and the EPO genomic coding sequence with modified 5'-UTR and minimal 3'-UTR (pSC2M-TKdhfr, Table 2. hereinbelow) and with the pASC2M-TKdhfr vector (Table 2, hereinbelow) which is similar to the pSC2M-TKdhfr vector however, devoid of the chimeric intron. As is shown in Table 2, hereinbelow, 48 hours post-transfection the level of secreted erythropoietin in the media was 140 IU/ml and 157 IU/ml in pSC2M-TKdhfr- and pASC2M-TKdhfr-transfected CHO cells, respectively.

TABLE 2

Production of recombinant EPO by transiently transfected CHO cells

| Expression Construct | IU/ml/48 hours | % of control (pC2-TKdhfr) |
|---|---|---|
| pC2-TKdhfr(control) | 98 | 100 |
| pSC2M-TKdhfr | 140 | 143 |
| pASC2M-TKdhfr | 157 | 161 |

Table 2: The amount of recombinant EPO secreted into the medium by CHO cells transfected with the various expression vectors is presented.
IU = International units.

When the expression level of EPO obtained using the teachings of the present invention was compared with the expression level obtained using prior art methods [Powell, J. S., 1986, U.S. Pat. No. 5,688,679 and Park, J. H. et al., Biotechnol. Appl. Biochem. (2000) 32, 167-72] it was found that the expression level of EPO in pASC2M-TKdhfr-transfected CHO cells was at least two times higher than the expression level of EPO generated using prior art approaches.

Thus, these results demonstrate that the erythropoietin construct of the present invention having a modified 5'-UTR and a shorter 3'-UTR is capable of producing high amounts of erythropoietin which can be used for therapeutic and research applications.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each

What is claimed is:

1. A chimeric polynucleotide comprising a nucleic acid sequence encoding an erythropoietin polypeptide attached to a 5'-UTR sequence, wherein said 5'-UTR sequence comprises SEQ ID NO:6 or 7.

2. The chimeric polynucleotide of claim 1, wherein said nucleic acid sequence includes an adenine as part of a guanine-guanine-adenine triplet encoding glycine at position 2 of said erythropoietin polypeptide.

3. The chimeric polynucleotide of claim 1, wherein said nucleic acid sequence comprises SEQ ID NO:11.

4. The chimeric polynucleotide of claim 1, wherein said nucleic acid sequence comprises SEQ ID NO:12.

5. The chimeric polynucleotide of claim 1, further comprising a promoter for directing expression of the chimeric polynucleotide in eukaryotic cells.

6. The chimeric polynucleotide of claim 5, further comprising a dihydrofolate reductase expression cassette positioned under a control of a thymidine kinase promoter.

7. The chimeric polynucleotide of claim 1, further comprising a promoter for directing expression of the chimeric polynucleotide in mammalian cells.

8. The chimeric polynucleotide of claim 7, wherein said promoter is selected from the group consisting of SV40 promoter, CMV promoter, adenovirus major late promoter, and Rous sarcoma virus promoter.

9. An isolated eukaryotic cell comprising the chimeric polynucleotide of claim 1.

10. The cell of claim 9, which is of mammalian origin.

11. The chimeric polynucleotide of claim 1, wherein said 5'-UTR sequence consists of SEQ ID NO:6 or 7.

* * * * *

SEQUENCE LISTING

<160> NUMBER OF SEQ ID NOS: 13

<210> SEQ ID NO 1
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 1
atgaattccc ccggtgtggt caccc                                              25

<210> SEQ ID NO 2
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 2
catgccggcc ctcaagttgg ccctg                                              25

<210> SEQ ID NO 3
<211> LENGTH: 57
<212> TYPE: DNA
<213> ORGANISM: Artificial sequence
<220> FEATURE:
<223> OTHER INFORMATION: Single strand DNA oligonucleotide

<400> SEQUENCE: 3
aattcttttg ttttgttttc ttttgttttg tttccaccat gggagtgcac ggtgagt          57

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4
accccaaacc aagtgccagg ttcct                                              25

<210> SEQ ID NO 5
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 5
tactcgagga cacacctggt catctgtc                                           28

<210> SEQ ID NO 6
<211> LENGTH: 23
<212> TYPE: DNA
<213> ORGANISM: Artificial sequence
<220> FEATURE:
<223> OTHER INFORMATION: A 5' UTR sequence capable of improving
      translational efficiency of fused human erythropoietin

<400> SEQUENCE: 6

-continued

| | | |
|---|---|---|
| ttttcttttg ttttgtttcc acc | | 23 |

<210> SEQ ID NO 7
<211> LENGTH: 38
<212> TYPE: DNA
<213> ORGANISM: Artificial sequence
<220> FEATURE:
<223> OTHER INFORMATION: A long form of a modified 5'UTR sequence

<400> SEQUENCE: 7

| | | |
|---|---|---|
| aattcttttg ttttgttttc ttttgttttg tttccacc | | 38 |

<210> SEQ ID NO 8
<211> LENGTH: 2428
<212> TYPE: DNA
<213> ORGANISM: Homo sapiens

<400> SEQUENCE: 8

| | | |
|---|---|---|
| cccccggtgt ggtcacccgg cgcgccccag gtcgctgagg gaccccggcc aggcgcggag | | 60 |
| atggggtgc acggtgagta ctcgcgggct gggcgctccc gccgcccgg gtccctgttt | | 120 |
| gagcggggat ttagcgcccc ggctattggc caggaggtgc ctgggttcaa ggaccggcga | | 180 |
| cttgtcaagg accccggaag ggggaggggg gtggggcagc ctccacgtgc cagcggggac | | 240 |
| ttgggggagt ccttggggat ggcaaaaacc tgacctgtga aggggacaca gtttgggggt | | 300 |
| tgaggggaag aaggtttggg ggttctgctg tgccagtgga gaggaagctg ataagctgat | | 360 |
| aacctgggcg ctggagccac cacttatctg ccagagggga agcctctgtc acaccaggat | | 420 |
| tgaagtttgg ccggagaagt ggatgctggt agctgggggt ggggtgtgca cacggcagca | | 480 |
| ggattgaatg aaggccaggg aggcagcacc tgagtgcttg catggttggg acaggaagg | | 540 |
| acgagctggg gcagagacgt ggggatgaag gaagctgtcc ttccacagcc acccttctcc | | 600 |
| ctccccgcct gactctcagc ctggctatct gttctagaat gtcctgcctg gctgtggctt | | 660 |
| ctcctgtccc tgctgtcgct ccctctgggc ctcccagtcc tgggcgcccc accacgcctc | | 720 |
| atctgtgaca gccgagtcct ggagaggtac ctccttgagg ccaaggaggc cgagaatatc | | 780 |
| acggtgagac cccttcccca gcacattcca cagaactcac gctcagggct tcaggaact | | 840 |
| cctcccagat ccaggaacct ggcacttggt tggggtggga gctgggaagc tagacactgc | | 900 |
| cccccctacat aagaataagt ctggtggccc caaaccatac ctggaaacta ggcaaggagc | | 960 |
| aaagccagca gatcctacgg cctgtgggcc agggccagag ccttcaggga cccttgactc | | 1020 |
| cccgggctgt gtgcatttca gacgggctgt gctgaacact gcagcttgaa tgagaatatc | | 1080 |
| actgtcccag acaccaaagt taatttctat gcctggaaga ggatggaggt gagttccttt | | 1140 |
| tttttttttt ttcctttctt ttggagaatc tcatttgcga gcctgatttt ggatgaaagg | | 1200 |
| gagaatgatc gagggaaagg taaaatggag cagcagagat gaggctgcct gggcgcagag | | 1260 |
| gctcacgtct ataatcccag gctgagatgg ccgagatggg agaattgctt gagccctgga | | 1320 |
| gtttcagacc aacctaggca gcatagtgag atccccatc tctacaaaca tttaaaaaaa | | 1380 |
| ttagtcaggt gaagtggtgc atggtggtag tcccagatat ttggaaggct gaggcgggag | | 1440 |
| gatcgcttga gcccaggaat tgaggctgc agtgagctgt gatcacacca ctgcactcca | | 1500 |
| gcctcagtga cagagtgagg ccctgtctca aaaagaaaa gaaaaaagaa aataatgag | | 1560 |
| ggctgtatgg aatacattca ttattcattc actcactcac tcactcattc attcattcat | | 1620 |
| tcattcaaca agtcttattg cataccttct gtttgctcag cttggtgctt ggggctgctg | | 1680 |

| | |
|---|---|
| aggggcagga gggagagggt gacatgggtc agctgactcc cagagtccac tccctgtagg | 1740 |
| tcgggcagca ggccgtagaa gtctggcagg gcctggccct gctgtcggaa gctgtcctgc | 1800 |
| ggggccaggc cctgttggtc aactcttccc agccgtggga gccctgcag ctgcatgtgg | 1860 |
| ataaagccgt cagtggcctt cgcagcctca ccactctgct tcgggctctg ggagcccagg | 1920 |
| tgagtaggag cggacacttc tgcttgccct ttctgtaaga aggggagaag ggtcttgcta | 1980 |
| aggagtacag gaactgtccg tattccttcc ctttctgtgg cactgcagcg acctcctgtt | 2040 |
| ttctccttgg cagaaggaag ccatctcccc tccagatgcg gcctcagctg ctccactccg | 2100 |
| aacaatcact gctgacactt tccgcaaact cttccgagtc tactccaatt tcctccgggg | 2160 |
| aaagctgaag ctgtacacag ggaggcctg caggacaggg gacagatgac caggtgtgtc | 2220 |
| cacctgggca tatccaccac ctccctcacc aacattgctt gtgccacacc ctcccccgcc | 2280 |
| actcctgaac cccgtcgagg ggctctcagc tcagcgccag cctgtcccat ggacactcca | 2340 |
| gtgccagcaa tgacatctca ggggccagag gaactgtcca gagcaact ctgagatcta | 2400 |
| aggatgtcac agggccaact tgagggcc | 2428 |

<210> SEQ ID NO 9
<211> LENGTH: 2184
<212> TYPE: DNA
<213> ORGANISM: Homo sapiens

<400> SEQUENCE: 9

| | |
|---|---|
| ttttcttttg ttttgtttcc accatgggag tgcacggtga gtactcgcgg gctgggcgct | 60 |
| cccgcccgcc cgggtccctg tttgagcggg gatttagcgc cccggctatt ggccaggagg | 120 |
| tggctggggtt caaggaccgg cgacttgtca aggaccccgg aagggggagg ggggtggggc | 180 |
| agcctccacg tgccagcggg gacttggggg agtccttggg gatggcaaaa acctgacctg | 240 |
| tgaagggggac acagtttggg ggttgagggg aagaaggttt gggggttctg ctgtgccagt | 300 |
| ggagaggaag ctgataagct gataacctgg gcgctggagc caccacttat ctgccagagg | 360 |
| ggaagcctct gtcacaccag gattgaagtt tggccggaga agtggatgct ggtagctggg | 420 |
| ggtggggtgt gcacacggca gcaggattga atgaaggcca gggaggcagc acctgagtgc | 480 |
| ttgcatggtt ggggacagga aggacgagct ggggcagaga cgtggggatg aaggaagctg | 540 |
| tccttccaca gccaccctttc tccctccccg cctgactctc agcctggcta tctgttctag | 600 |
| aatgtcctgc ctggctgtgg cttctcctgt ccctgctgtc gctccctctg ggcctcccag | 660 |
| tcctgggcgc cccaccacgc ctcatctgtg acagccgagt cctggagagg tacctcttgg | 720 |
| aggccaagga ggccgagaat atcacggtga gacccttcc ccagcacatt ccacagaact | 780 |
| cacgctcagg gcttcaggga actcctccca gatccaggaa cctggcactt ggtttggggt | 840 |
| ggagctggga agctagacac tgccccccta cataagaata agtctggtgg ccccaaacca | 900 |
| tacctggaaa ctaggcaagg agcaaagcca gcagatccta cggcctgtgg gccagggcca | 960 |
| gagccttcag ggacccttga ctccccgggc tgtgtgcatt tcagacgggc tgtgctgaac | 1020 |
| actgcagctt gaatgagaat atcactgtcc cagacaccaa agttaatttc tatgcctgga | 1080 |
| agaggatgga ggtgagttcc tttttttttt ttttccttt cttttggaga atctcatttg | 1140 |
| cgagcctgat tttggatgaa agggagaatg atcgaggaa aggtaaaatg gagcagcaga | 1200 |
| gatgaggctg cctgggcgca gaggctcacg tctataatcc caggctgaga tggccgagat | 1260 |
| gggagaattg cttgagccct ggagtttcag accaacctag gcagcatagt gagatccccc | 1320 |
| atctctacaa acatttaaaa aaattagtca ggtgaagtgg tgcatggtgg tagtcccaga | 1380 |

```
tatttggaag gctgaggcgg gaggatcgct tgagcccagg aatttgaggc tgcagtgagc    1440
tgtgatcaca ccactgcact ccagcctcag tgacagagtg aggccctgtc tcaaaaaaga    1500
aaagaaaaaa gaaaataat gagggctgta tggaatacat tcattattca ttcactcact     1560
cactcactca ttcattcatt cattcattca acaagtctta ttgcatacct tctgtttgct    1620
cagcttggtg cttggggctg ctgaggggca ggagggagag ggtgacatgg gtcagctgac    1680
tcccagagtc cactccctgt aggtcgggca gcaggccgta gaagtctggc agggcctggc    1740
cctgctgtcg gaagctgtcc tgcggggcca ggccctgttg gtcaactctt cccagccgtg    1800
ggagcccctg cagctgcatg tggataaagc cgtcagtggc cttcgcagcc tcaccactct    1860
gcttcgggct ctgggagccc aggtgagtag gagcggacac ttctgcttgc cctttctgta    1920
agaaggggag aagggtcttg ctaaggagta caggaactgt ccgtattcct tccctttctg    1980
tggcactgca gcgacctcct gttttctcct tggcagaagg aagccatctc ccctccagat    2040
gcggcctcag ctgctccact ccgaacaatc actgctgaca ctttccgcaa actcttccga    2100
gtctactcca atttcctccg gggaaagctg aagctgtaca cagggaggc ctgcaggaca     2160 ggggacagat gaccaggtgt gtcc                                           2184
```

<210> SEQ ID NO 10
<211> LENGTH: 193
<212> TYPE: PRT
<213> ORGANISM: Homo sapiens

<400> SEQUENCE: 10

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 11
<211> LENGTH: 582
<212> TYPE: DNA

<213> ORGANISM: Homo sapiens

<400> SEQUENCE: 11

| | | | | | |
|---|---|---|---|---|---|
| atgggggtgc | acgaatgtcc | tgcctggctg | tggcttctcc | tgtccctgct | gtcgctccct | 60 |
| ctgggcctcc | cagtcctggg | cgccccacca | cgcctcatct | gtgacagccg | agtcctggag | 120 |
| aggtacctct | tggaggccaa | ggaggccgag | aatatcacga | cgggctgtgc | tgaacactgc | 180 |
| agcttgaatg | agaatatcac | tgtcccagac | accaaagtta | atttctatgc | ctggaagagg | 240 |
| atggaggtcg | ggcagcaggc | cgtagaagtc | tggcagggcc | tggccctgct | gtcggaagct | 300 |
| gtcctgcggg | gccaggccct | gttggtcaac | tcttcccagc | cgtgggagcc | cctgcagctg | 360 |
| catgtggata | aagccgtcag | tggccttcgc | agcctcacca | ctctgcttcg | ggctctggga | 420 |
| gcccagaagg | aagccatctc | ccctccagat | gcggcctcag | ctgctccact | ccgaacaatc | 480 |
| actgctgaca | ctttccgcaa | actcttccga | gtctactcca | atttcctccg | ggaaagctg | 540 |
| aagctgtaca | caggggaggc | ctgcaggaca | ggggacagat | ga | | 582 |

<210> SEQ ID NO 12
<211> LENGTH: 2149
<212> TYPE: DNA
<213> ORGANISM: Homo sapiens

<400> SEQUENCE: 12

| | | | | | |
|---|---|---|---|---|---|
| atgggggtgc | acggtgagta | ctcgcgggct | gggcgctccc | gcccgccgg | gtccctgttt | 60 |
| gagcggggat | ttagcgcccc | ggctattggc | caggaggtgg | ctgggttcaa | ggaccggcga | 120 |
| cttgtcaagg | accccggaag | ggggaggggg | gtggggcagc | ctccacgtgc | cagcggggac | 180 |
| ttggggagt | ccttggggat | ggcaaaaacc | tgacctgtga | agggacacga | gtttgggggt | 240 |
| tgaggggaag | aaggtttggg | ggttctgctg | tgccagtgga | gaggaagctg | ataagctgat | 300 |
| aacctgggcg | ctggagccac | cacttatctg | ccagagggga | agcctctgtc | acaccaggat | 360 |
| tgaagtttgg | ccggagaagt | ggatgctggt | agctgggggt | ggggtgtgca | cacggcagca | 420 |
| ggattgaatg | aaggccaggg | aggcagcacc | tgagtgcttg | catggttggg | gacaggaagg | 480 |
| acgagctggg | gcagagacgt | ggggatgaag | gaagctgtcc | ttccacagcc | acccttctcc | 540 |
| ctccccgcct | gactctcagc | ctggctatct | gttctagaat | gtcctgcctg | gctgtggctt | 600 |
| ctcctgtccc | tgctgtcgct | ccctctgggc | ctccagtcc | tgggcgcccc | accacgcctc | 660 |
| atctgtgaca | gccgagtcct | ggagaggtac | ctcttggagg | ccaaggaggc | cgagaatatc | 720 |
| acggtgagac | cccttcccca | gcacattcca | cagaactcac | gctcagggct | tcagggaact | 780 |
| cctcccagat | ccaggaacct | ggcacttggt | ttggggtgga | gctgggaagc | tagacactgc | 840 |
| cccctacat | aagaataagt | ctggtggccc | caaaccatac | ctggaaacta | ggcaaggagc | 900 |
| aaagccagca | gatcctacgg | cctgtgggcc | agggccagag | ccttcaggga | cccttgactc | 960 |
| cccgggctgt | gtgcatttca | gacgggctgt | gctgaacact | gcagcttgaa | tgagaatatc | 1020 |
| actgtcccag | acaccaaagt | taatttctat | gcctggaaga | ggatggaggt | gagttccttt | 1080 |
| ttttttttt | ttcctttctt | ttggagaatc | tcatttgcga | gcctgatttt | ggatgaaagg | 1140 |
| gagaatgatc | gagggaaagg | taaaatggag | cagcagagat | gaggctgcct | gggcgcagag | 1200 |
| gctcacgtct | ataatcccag | ctgagatggc | cgagatggga | agaattgctt | gagccctgga | 1260 |
| gtttcagacc | aacctaggca | gcatagtgag | atcccccatc | tctacaaaca | tttaaaaaaa | 1320 |
| ttagtcaggt | gaagtggtgc | atggtggtag | tcccagatat | ttgaaggct | gaggcgggag | 1380 |
| gatcgcttga | gcccaggaat | ttgaggctgc | agtgagctgt | gatcacacca | ctgcactcca | 1440 |

```
gcctcagtga cagagtgagg ccctgtctca aaaaagaaaa gaaaaagaa aaataatgag   1500
ggctgtatgg aatacattca ttattcattc actcactcac tcactcattc attcattcat   1560
tcattcaaca agtcttattg catacctcct gtttgctcag cttggtgctt ggggctgctg   1620
aggggcagga gggagagggt gacatgggtc agctgactcc cagagtccac tccctgtagg   1680
tcggggcagca ggccgtagaa gtctggcagg cctggccct gctgtcggaa gctgcctgc    1740
ggggccaggc cctgttggtc aactcttccc agccgtggga gcccctgcag ctgcatgtgg   1800
ataaagccgt cagtggcctt cgcagcctca ccactctgct tcgggctctg ggagcccagg   1860
tgagtaggag cggacacttc tgcttgccct ttctgtaaga aggggagaag ggtcttgcta   1920
aggagtacag gaactgtccg tattccttcc ctttctgtgg cactgcagcg acctcctgtt   1980
ttctccttgg cagaaggaag ccatctcccc tccagatgcg gcctcagctg ctccactccg   2040
aacaatcact gctgacactt tccgcaaact cttccgagtc tactccaatt tcctccgggg   2100
aaagctgaag ctgtacacag gggaggcctg caggacaggg gacagatga             2149

<210> SEQ ID NO 13
<211> LENGTH: 2198
<212> TYPE: DNA
<213> ORGANISM: Mus musculus

<400> SEQUENCE: 13
ggcggggcct aagctgcgca agtggtacac agctcagggc tgcgatttcg cgccaaactt     60
gacggcaatc ctagcgtgaa ggctggtagg attttatccc cgctgccatc atggttcgac    120
cattgaactg catcgtcgcc gtgtcccaaa atatggggat tggcaagaac ggagacctac    180
cctggcctcc gctcaggaac gagttcaagt acttccaaag aatgaccaca acctcttcag    240
tggaaggtaa acagaatctg gtgattatgg gtaggaaaac ctggttctcc attcctgaga    300
agaatcgacc tttaaaggac agaattaata tagttctcag tagagaactc aaagaaccac    360
cacgaggagc tcatttttctt gccaaaagtt tggatgatgc cttaagactt attgaacaac    420
cggaattggc aagtaaagta gacatggttt ggatagtcgg aggcagttct gtttaccagg    480
aagccatgaa tcaaccaggc cacctcagac tctttgtgac aaggatcatg caggaatttg    540
aaagtgcacac gtttttccca gaaattgatt tggggaaata taaacttctc ccagaatacc    600
caggcgtcct ctctgaggtc caggaggaaa aaggcatcaa gtataagttt gaagtctacg    660
agaagaaaga ctaacaggaa gatgctttca agttctctgc tcccctccta aagctatgca    720
tttttataag accatgggac ttttgctggc tttagatcta tgagtaatta tttcttagg     780
gagggggtagt tggaagaatt gtttgttttg tgatcctggg gatggaacct aagacccagt    840
gcgtgctgag caaatgctat actgctgagc cacccccaacc ctagccccta tataattcta    900
aacaatatgt tgtcatttcc cagtaatcta acaaggttat agtaaaagtg ccttaagaaa    960
tgtcacttgc tataaaggtc tcagtgcccc tcccatgaga cctcaagtgg ctccccagca   1020
tatgcacagg gtactgtgtg tacaagagac cccagtgatg tagagcccct ggagcatgag   1080
cagatgtgtg ggctcataaa agtaggagct aggcaggtaa gtccaaaggg cagaaacagg   1140
ttttaaacag cagagctgga actcagacta taaagaaaat tccatcaaag tagagactgg   1200
attattgtat gcacatcaca cttgcagcaa agctctgctc actcagacag aaaatcagta   1260
aatggagaac tccattgtgt tccatggaga cgagagcagg tggaagatta tgtaagatct   1320
gaaacactga aattgtctgc ttctcatctt cagtgagatt ccaaaggata gtacagtgac   1380
```

-continued

```
agaacaagaa taggcactct ctacaaaaaa aagaaagaaa aaactaagta atagcaagca    1440
taatagctac tgttaagaac tcagagataa tgaattgaga atggatactg cttgaaatga    1500
aaatttaata agttagaaac taaactttat aaaaataaaa aaatgagcat taaaatggct    1560
ttcctcatct cagcagggtt tcagatcatc aggtcagaga aagtatttct gcctggcctt    1620
gtaaattagt atggtctttt tttatctttt acttgacaat ttcctacatt tttacgatgt    1680
gtcttaatca taccaggtcc tcatccccac tccccacta cctttgtatc ttctttctct     1740
tttcataacc ttctgaaacc agtcattgct ttcttcatgt tcctgcatgt gtgctgtcca    1800
ctggagtacg ggcagcctgc cagtggacac acacacacac acacacacac acacacacac    1860
acacacacac agagccatca gttaccaata gctcttcagc tgggtgcagt cttaggagcc    1920
tctcctccat ccaagctaga atatgggtct gcagatcacc acagctgctg tgagcttgtg    1980
agtgtggtgt ccatgccatg tccagaaggc agcattatat atacatggcc ctattcccca    2040
ggcttcaggc cttcattctt tccaccactt cttcagtgct ccctgagcct tagacaagtc    2100
tactgataga aatggtctgt tcagagctga atagtaaaca gtcacttagt ctctacactt    2160
tgatcagcct tgtgtctgta agctggatgc tctctacc                            2198
```